United States Patent
Noh et al.

(10) Patent No.: US 7,241,589 B2
(45) Date of Patent: Jul. 10, 2007

(54) METHOD FOR PREPARATION OF ANDROST-4-ENE-3,17-DIONE AND ANDROSTA-1,4-DIENE-3,17-DIONE

(75) Inventors: Seung-Kwon Noh, Seoul (KR); Myung-Kuk Kim, Seoul (KR); Won-Tae Yoon, Seoul (KR); Kyung-Moon Park, Gyeonggi-do (KR); Sang-Ok Park, Seoul (KR)

(73) Assignee: Eugene Science Inc., Seoul (KR)

( * ) Notice: Subject to any disclaimer, the term of this patent is extended or adjusted under 35 U.S.C. 154(b) by 519 days.

(21) Appl. No.: 10/477,448

(22) PCT Filed: May 10, 2002

(86) PCT No.: PCT/KR02/00876

§ 371 (c)(1),
(2), (4) Date: Nov. 10, 2003

(87) PCT Pub. No.: WO02/092830

PCT Pub. Date: Nov. 21, 2002

(65) Prior Publication Data

US 2004/0152153 A1    Aug. 5, 2004

(30) Foreign Application Priority Data

May 11, 2001  (KR) .............................. 2001-25704

(51) Int. Cl.
*C12P 33/00* (2006.01)
(52) U.S. Cl. ...................... 435/52; 435/253.1; 435/244
(58) Field of Classification Search ..................... None
See application file for complete search history.

(56) References Cited

U.S. PATENT DOCUMENTS

| 4,097,334 | A |   | 6/1978 | Weber et al. |
| 4,212,940 | A | * | 7/1980 | Weber et al. .................. 435/55 |
| 4,397,946 | A | * | 8/1983 | Imada et al. .................. 435/55 |
| 4,528,271 | A | * | 7/1985 | Udvardy Nagy nee Cserey Pechany et al. ... 435/55 |
| 5,418,145 | A | * | 5/1995 | Weber et al. ............... 435/555 |

FOREIGN PATENT DOCUMENTS

| JP | 57-08794 A | 1/1982 |
| WO | WO 87-03620 A | 6/1987 |

* cited by examiner

*Primary Examiner*—Irene Marx
(74) *Attorney, Agent, or Firm*—Drinker Biddle & Reath LLP; Daniel A. Monaco

(57) ABSTRACT

The present invention relates to a method for preparation of androst-4-ene-3,17-dione (AD) and androsta-1,4-diene-3,17-dione (ADD). More particularly, the present invention relates to a method for preparing AD/ADD, comprising the steps of: (a) heating sterols and emulsifier respectively, to dissolve completely and mixing to prepare a mixture; (b) placing the mixture in a water bath at 70~90° C. and stirring to obtain emulsified sterols; and (c) adding the emulsified sterols to culture media of microorganism as a component. And the present invention relates to a method for preparing AD/ADD, comprising the addition of cyclodextrin-sterol complexes extracted from milk to culture media of microorganism as a component. The emulsified sterols and cyclodextrin-sterol complexes adopted in the present invention can be easily prepared and be effectively used for obtaining AD/ADD at a high yield.

4 Claims, No Drawings

METHOD FOR PREPARATION OF ANDROST-4-ENE-3,17-DIONE AND ANDROSTA-1,4-DIENE-3,17-DIONE

TECHNICAL FIELD

The present invention relates to a method for preparation of androst-4-ene-3,17-dione (hereinafter, referred to as "AD") and androsta-1,4-diene-3,17-dione (hereinafter, referred to as "ADD"). More particularly, the present invention relates to a method for preparing AD/ADD at a high yield in which emulsified sterol or cyclodextrin-sterol complex is used as a component of a culture medium for microorganisms.

PRIOR ART

Steroids, which are secretary hormones released from the adrenal cortex, the testicle, the ovary or the placenta and the corpus luteum are synthesized from cholesterol in a human body. They are classified into about five classes according to their physiological activities, as follows: sex hormones of androgen (androsterone, testosterone, etc.) and estrogen (estradiol, etc.) playing a critical role in the development of secondary sex characteristics in men and women, respectively, gestogen (progesterone, etc.) stimulating and maintaining pregnancy, glucocorticoid (cortisone, hydrocortisone, etc.) stimulating gluconeogenesis and increasing liver glycogen levels by catabolism of proteins, and mineralcorticoid (deoxycorticosterone, aldosterone, etc.) playing an important role in maintaining the balance of electrolytes and water in a body.

Levels of the above hormones become unbalanced in a body owing to increased stresses and exposure to environmental hormones in accordance with the advance of civilization, resulting in occurrence of many diseases, and widespread use of the steroid hormones is conducted for therapy of the diseases. In particular, synthesized estrogens are essentially used in artificial fertilization and therapy of sterile patients, and glucocorticoids play a role in relieving the pain caused by various inflammations, such as iriditis, arthritis and the like. In addition, Addison's disease, which is fatal, can be treated by administration of deoxycorticosterone and hydrocortisone.

There have been conducted a variety of researches into in vitro synthesis of steroid hormones to meet the increased demands as described above, among them, the method for preparing AD/ADD as a precursor to obtain steroid hormones is generally exploited. The AD/ADD are manufactured through the metabolic process of sterols using oxidative enzymes of microorganisms. At this moment, as a substrate, cholesterol, sitosterol, campesterol, stigmasterol, ergosterol, their sterol oxides and the like can be utilized. However, since these substances are hydrophobic, there are limitations for improving the availability of substrates in microorganisms. Therefore, in order to solve the problem, various methods to enhance the productivity of AD and ADD by increasing the availability for microorganisms have been performed.

Hesseline and his associates have increased the degradation of lateral chains in steroids by using *Mycobacterium* sp. strains, in which cyclodextrin is added as a collector of sterols onto culture broth in order to dissolve insoluble sterols in water soluble media, resulting in a twice higher conversion rate of sterols into AD and ADD than previously known (Paul G. M. Hesselink, et al., Enzyme Microbiology and Technology, 1989, 11, 398–404).

Lee and his colleagues have added an organic solvent, such as 2% acetone to improve the dispersion rate of steroids within culture media and have proceeded with two steps using two kinds of microorganisms to increase conversion yield of sterols into AD/ADD (Chung-Yi Lee, et al., Applied Microbiology and Biotechnology, 1993, 38, 447–452). consequently, the AD/ADD yield was estimated to be higher in the case when organic solvent was used than not used. But, there is a disadvantage that sterol solution is difficult to prepare to more than 1% of concentration when 2% acetone is added.

Lee Gang Min and his associates have adopted a method for exploiting a micro-emulsion in order to increase the availability of sterols as a substrate (J. of Korean Biological Engineering, Vol. 7, No. 3, 161–165). Concretely, sitosterol, as a kind of sterol was cross-linked with glutaldehyde and then made to a micro-emulsion by using a detergent. The obtained micro-emulsion was added to a culture medium. As a result, a maximum of 120 mg of AD/ADD per 1 g of cell weight was obtained in the case where 3 g of sitosterol was utilized.

Sedlaczek and his colleagues have tried to increase the use of sterols, wherein glycine as an inhibitor working on cell walls is added to a culture medium. This reduces cross-linkages among peptides of the cell wall and degrades peptidoglycan bonds (L. Sedlaczek, et al., Applied Microbiology and Biotechnology, 1999, Vol. 52, 563–571). As a result, the cell growth was confirmed to decrease, but the yield of AD/ADD, increased to about 10%.

Goetschel and his associates have cultivated *Rhodococcus erythropolis* onto liposomal media in order to enhance the oxidation of cholesterols (Ruth Goetschel, et al., Enzyme Microbiology and Technology, 1992, Vol. 14, 390–395).

Furthermore, Wang and her colleagues have adopted a mutant strain which is blocked in the biosynthesis of mycolic acid, a major component of cell wall in *Mycobacterium* and experimented with the conversion of sterol into hormone intermediates by using the mutant strain (Linda Wang, et al., The Journal of Biological Chemistry, 2000, Vol. 275, No. 10, 7224–7229). Belanger and her associates also have exploited mutant strains in which the dd1A gene relating to the peptidoglycan biosynthesis of *Mycobacterium smegmatis* is deleted so as to improve the utility of sterols (Aimee E. Belanger, et al., Journal of Bacteriology, 2000, Vol. 182, No. 23, 6854–6856).

As demonstrated above, although these methods have improved the conversion of sterols into AD/ADD, the ratio of increase was small. Therefore, novel methods are required to magnify the availability of sterols in microorganisms.

DISCLOSURE OF THE INVENTION

Hence, the inventors of the present invention have tried to develop a novel method. Consequently, we have found that if emulsified sterols or sterol-associated cyclodextrin is added to a culture medium during the cultivation, the productivity of AD/ADD can increase highly. Based upon this result, the present invention has been successfully completed.

Accordingly, it is an object of the present invention to provide a method for preparation of AD/ADD having increased productivity of AD/ADD by improving the availability of sterols in microorganisms.

To achieve the object, the present invention provides a method for preparing AD/ADD, comprising the steps of: (a) heating sterols and emulsifier respectively, dissolving completely and mixing to prepare a mixture; (b) placing the mixture in a water bath at 70~90° C. and stirring to obtain emulsified sterols; and (c) adding the emulsified sterols to culture media of microorganism as a component.

To achieve the object, the present invention provides another method for preparation of AD/ADD, comprising the addition of cyclodextrin-sterol complexes extracted from milk to culture media of microorganism as a component.

BEST MODE FOR CARRYING OUT THE INVENTION

Hereinafter, the present invention will be illustrated more clearly as follows.

The present invention provides a method for preparing AD/ADD at a high yield, in which emulsified sterols are added as a component of a culture medium for microorganisms.

To obtain the emulsified sterol of the present invention, at first, sterols and emulsifier, respectively, were heated to dissolve completely and then mixed. And then the mixture was placed in a water bath at 70~90° C. and stirred to obtain emulsified sterols. The reason why the above method is adopted is that sterols are an insoluble substance. If the sterols are emulsified in the emulsifier to which water is already added, the effectiveness of emulsification is reduced and on the contrary, if the sterols and the emulsifiers are mixed uniformly and then emulsified, the efficiency of emulsification can be maximized. Therefore, two substances are preferably mixed in a liquefied state.

The emulsifier useful in the present invention is selected from the group consisting of sucrose fatty acid ester, sorbitan fatty acid ester, polysorbate, polyglycerol fatty acid, propylene glycerol fatty acid and polyglycerine fatty acid ester. Particularly, sucrose fatty acid ester is preferable. The sterols and emulsifier are mixed at a weight ratio of 1:0.2~2.0 (w/w), preferably 1:0.1~1.0 (w/w). In the emulsified sterol solution, the concentration of sterols is at a weight ratio of 0.1~20% (w/v), preferably 1~10% (w/v).

The emulsified sterol solution is used at a weight of 0.01~10 g of sterols per 100 ml of a culture medium, preferably 0.1~5 g.

In addition, the present invention provides another method for preparing AD/ADD at a high yield, in which cyclodextrin-sterol complex is added as a component of a culture medium for microorganisms.

The cyclodextrin is extracted from milk, in which cholesterol is removed. Cyclodextrin is known as an additive exploited to manufacture low-cholesterol milk. The cholesterol removed from milk is retained in the form of cyclodextrin-cholesterol complexes.

Therefore, the cyclodextrin is an excellent substrate for the conversion in microorganisms since it is very economical in the cost, can be easily dissolved and dispersed into a culture medium being in an aqueous solution for microorganisms.

The cyclodextrin can be selected from the group consisting of α-cyclodextrin, β-cyclodextrin and γ-cyclodextrin. β-cyclodextrin is preferred since it is very strong in structural binding to sterols.

In case of the addition to a culture medium, the cyclodextrin-sterol complex can be used at a weight of 0.07~70 g per 100 ml of culture media and preferably, 0.7~35 g.

The microorganism useful in the present invention can be any strain that uses sterols as a carbon source. Precisely, the microorganism is selected from the group consisting of *Arthrobacter, Nocardia, Fusarium, Mycobacterium, Micro-bacterium, Protaminobacter, Brevibacterium, Corynebacterium, Bacillus, Serratia, Azotobacter, Streptomyces, Alkaligenes, Pseudomonas* and the like including their mutant strains. Furthermore, typical strains which belong to the above genus are *Arthrobacter* simplex IAM 1660, *Norcardia erythropolis* ATCC 4277, *Mycobacterium smegmatis* IFO 3083, *Mycobacterium phlei* IFO 3158, *Mycobacterium fortuitum, Protaminobacter alboflavus* ATCC 8458, *Brevibacterium lipolyticum* IAM 1398, *Corynebacterium equi* IAM 1038 and their mutant strains. Preferably, among these strains, *Arthrobacter* simplex, *Brevibacterium lipolyticum* and *Mycobacterium* sp. can be adopted. Also, it is more preferred to adopt *Mycobacterium fortuitum* EUG-119 strain deposited in Korean Culture Center of Microorganisms with accession No. KCCM 10259 on Apr. 14, 2001, which is prepared by performing mutagenesis from *Mycobacterium fortuitum* ATCC 29472, since the strain has an excellent conversion efficiency of sterols into AD/ADD.

The sterols used in the present invention are selected from the group consisting of cholesterol, sitosterol, campesterol, stigmasterol and ergosterol.

In the present invention, the productivity of AD/ADD according to the present method is examined and compared with that of conventional methods. Concretely, in case that cholesterol prepared according to the prior technique comprising homogenization with detergents using a mixer, ultrasonification and re-homogenization after addition of organic solvents is used to cultivate microorganisms, the productivity of AD/ADD is identified to be limited in the range of 40.6~51.7 mg/100 ml per 0.5 g/100 ml of cholesterol added. On the contrary, in case that the emulsified cholesterol of the present invention is used to cultivate microorganisms, the productivity of AD/ADD is identified to be 130 mg /100 ml per 0.5 g/100 ml of cholesterol added. Besides, in the case that the cyclodextrin-cholesterol extracted from milk is used to cultivate microorganisms, the productivity of AD/ADD is verified to reach 92.2 mg /100 ml per 0.5 g/100 ml of cholesterol added. The values estimated above in the amount of AD/ADD are about 2~3 times higher than that of the conventional method.

Consequently, the method of the present invention can be exploited efficiently in order to produce AD/ADD at a high yield.

The present invention will be explained in more detail with reference to the following examples. However, the following examples are provided only to illustrate the present invention, and the present invention is not limited to them.

EXAMPLE 1

Cultivation of Microorganism

In order to cultivate microorganisms, the procedure performed in the following examples was based on the method of Example 1, except for the kinds and quantity of cholesterol added during the cultivation.

The culture medium consisting of ingredients shown in Table 1 was prepared and adjusted to pH 7.0. 5 ml of the culture medium prepared above was poured into a tube, sterilized by using a high pressure at 120° C. for 15 minutes and cooled. *Mycobacterium fortuitum* ATCC 29472 was inoculated into the culture medium with a platinum loop. The inoculated culture medium was cultivated at 30° C. for 4 days at 200 rpm so as to prepare the seed culture solution.

TABLE 1

| Ingredient | Weight % |
|---|---|
| Yeast extract | 0.1% |
| Nutritional broth | 0.8% |
| Glycerol | 0.5% |
| Tween 80 | 0.01% |
| Water | add until 100 ml |

In the present cultivation, the main culture medium prepared according to the ingredients illustrated in Table 2, except glucose, was adjusted to pH 7.0. Then, 85 ml of the main culture medium for fermentation was put into a stirring flask with 500 ml volume and sterilized with a high pressure. Glucose was made to a solution with 10-fold concentration separately, sterilized and added to the main culture medium for the fermentation with 10 ml. At this moment, cholesterol was added by adjusting to a final concentration of 5 g/l in the culture medium.

Then, 5 ml of the obtained seed culture broth was inoculated into 95 ml of the main culture medium for the fermentation already completed, made to have the final volume of 100 ml and cultivated at 30° C. for 5 days at 200 rpm under a stirrer.

TABLE 2

| Ingredient | Weight (W %) |
|---|---|
| Glucose | 1% |
| Yeast extract | 0.5% |
| Potassium phosphate (dibasic) | 0.04% |
| Potassium phosphate (monobasic) | 0.08% |
| Magnesium sulfate | 0.02% |
| Iron sulfate (II) | 0.0005% |
| Ammonium nitrate | 0.15% |
| Zinc sulfate | 0.0002% |
| Manganese chloride | 0.00005% |
| Tween 80 | 0.05% |
| Water | Add until 1 L |

EXAMPLE 2

The following procedure was performed in order to examine the variation of ADD quantities produced in the case of cyclodextrin-cholesterol complex extracted from milk.

5 kg of β-cyclodextrin was added to 500 L of milk and then homogenized at 4° C. for 10 minutes at 500 rpm using a homo-mixer. The homogenized milk solution was centrifuged at 4° C. for 5 minutes at 6,000 rpm, obtaining cholesterol-cyclodextrin complex. The obtained cholesterol-cyclodextrin complex was diluted to reach a concentration of 50 g/L of cholesterol by using water and was then homogenized with the homo-mixer again. 10 m. of the cholesterol-cyclodextrin complex solution prepared finally (at a concentration of 50 g/L of cholesterol) and 5 ml of the seed culture broth were added to the main culture medium for fermentation and cultivated through the method described in the above Example 1.

In order to examine the AD/ADD quantity produced, 1 ml of the culture broth was extracted twice with 4 ml of a mixture of ethyl ether and petroleum ether in a ratio of 1:1, evaporated under reduced pressure and dissolved with 2-propanol to perform high pressure liquid chromatography analysis.

As a result, AD/ADD was obtained at an amount of 92.2 mg/100 ml per 0.5 g/100 ml of cholesterol.

EXAMPLE 3

Cholesterol was used in the emulsified state prepared previously according to the present invention. Cholesterol and a sucrose fatty acid ester (emulsifier) were respectively heated to a melting point, dissolved completely, mixed at a weight ratio of 1: 0.5 (w/w; cholesterol: emulsifier) and stirred within water at 80° C. to make the emulsified cholesterol.

10 ml of the emulsified cholesterol solution (50 g/L of cholesterol) prepared through the above procedure and 5 ml of the seed culture solution were added to the main culture medium for the fermentation arid cultivated through the method described in Example 1. The quantity of AD/ADD obtained in the cultivated medium was measured through the method described in Example 2.

As a result, AD/ADD was obtained at an amount of 130 mg/100 ml per 0.5 g/100 ml of cholesterol added.

EXAMPLE 4

Seed culture broth was prepared by performing the method described in Example 1 except for using *Mycobacterium fortuitum* EUG-119 (KCCM-10259) as a microorganism.

10 ml of the cholesterol-cyclodextrin complex solution prepared finally (at a concentration of 50 g/L of cholesterol) through the method described in Example 2 and 5 ml of the seed culture broth were added to the main culture medium for the fermentation and cultivated through the method described in the Example 1. The quantity of AD/ADD obtained in the cultivated medium was measured through the method described in Example 2.

As a result, AD/ADD was obtained at an amount of 228.8 mg/100 ml per 0.5 g/100 ml of cholesterol added.

EXAMPLE 5

10 ml of the emulsified cholesterol solution (50 g/L of cholesterol) prepared through the method described in Example 3 and 5 ml of the seed culture broth of the Example 4 were added to the main culture medium for the fermentation and cultivated through the method described in Example 1. The quantity of AD/ADD obtained in the cultivated medium was measured through the method described in Example 2.

As a result, AD/ADD was obtained at an amount of 258.3 mg/100 ml per 0.5 g/100 ml of cholesterol added.

COMPARATIVE EXAMPLE 1

Cholesterol homogenized after mixing with a detergent was used to cultivate microorganisms. First, 0.05 weight % of Tween 80 as a detergent was added to 5 g of cholesterol. The whole volume was increased to 100 ml using water, so as to prepare a mixed solution. Then, the mixed solution was homogenized with a homo-mixer at 5,000 rpm for 20 minutes. 10 ml of the homogenized cholesterol solution (at a concentration of 50 g/L of cholesterol) and 5 ml of the seed culture broth (Example 1) were added to the main culture medium for the fermentation and cultivated. Then, the AD/ADD quantity was measured through the method described in Example 2.

COMPARATIVE EXAMPLE 2

A detergent and cholesterol grinded with an ultrasonicator were used.

The mixed solution of which whole volume runs to 100 ml was made of 5 g of cholesterol added with 0.5 weight % of Tween 80 and water. The mixed solution was grinded with an ultrasonicator for 20 minutes. 10 ml of the grinded cholesterol solution (at a concentration of 50 g/L of cholesterol) and 5 ml of the seed culture broth (Example 1) were added to the main culture medium for the fermentation and cultivated. Thereafter, AD/ADD quantity was measured through the method described in Example 2.

Consequently, AD/ADD was obtained at an amount of 44.3 mg/100 ml per 0.5 g/100 ml of cholesterol added. The yield of AD/ADD in this Comparative Example was the same as that of Comparative Example 1, confirming that the utility of the microorganisms was not effective in the case of using cholesterol treated with a homo-mixer or an ultrasonicator

COMPARATIVE EXAMPLE 3

Homogenized cholesterol added to a surfactant and an organic solvent was used. A mixed solution of which whole volume runs to 100 ml was made of 5 g of cholesterol added to 0.05 weight % of Tween 80, 20 ml of acetone, and water. The mixed solution was homogenized using a homo-mixer at 500 rpm for 20 minutes. 10 ml of the homogenized cholesterol solution (at a concentration of 50 g/L of cholesterol) and 5 ml of the seed culture broth (Example 1) were added to the main culture medium for fermentation and cultivated. Thereafter, AD/ADD quantity was measured through the method described in Example 2.

As a result, AD/ADD was obtained at an amount of 51.7 mg/100 ml per 0.5 g/100 ml of cholesterol added.

COMPARATIVE EXAMPLE 4

Cholesterol added to a surfactant and dispersed in an organic solvent was used. A mixed solution of which whole volume runs to 100 ml was made from 5 g of cholesterol added to 0.05 weight % of Tween 80, 20 ml of acetone, and water. 10 ml of the dispersed cholesterol solution (at a concentration of 50 g/L of cholesterol) and 5 ml of the seed culture broth (Example 1) were added to the main culture medium for fermentation and cultivated. Thereafter, AD/ADD quantity was measured through the method described in Example 2.

As a result, AD/ADD was obtained at an amount of 40.6 mg/100 ml per 0.5 g/100 ml of cholesterol added.

Results from the above Examples and Comparative Examples are shown in Table 3.

TABLE 3

| No. of Ex. | Method used | Quantity (mg/L) | Conversion ratio (%) |
|---|---|---|---|
| Example 2 | Cholesterol-Cyclodextrin complex | 922 | 25 |
| Example 3 | Emulsified cholesterol | 1,300 | 35 |
| Example 4 | Cholesterol-Cyclodextrin complex | 2,288 | 62 |
| Example 5 | Emulsified cholesterol | 2,583 | 70 |
| Comparative Example 1 | Homogenization | 443 | 12 |
| Comparative Example 2 | Ultrasonification | 443 | 12 |
| Comparative Example 3 | Homogenization-Organic solvent | 517 | 14 |
| Comparative Example 4 | Organic solvent | 406 | 11 |

As shown in Table 3, the yield of AD/ADD in obtained using emulsified cholesterol and cholesterol-cyclodextrin complexes of the present invention is two to six times higher than the yield obtained using conventional methods.

INDUSTRIAL APPLICABILITY

As described above, the emulsified cholesterol and cyclodextrin-cholesterol complex of the present invention can be easily prepared and be effectively used for obtaining AD/ADD at a high yield as shown in the above examples.

The invention claimed is:

1. A method, for preparing androst-4-ene-3,17-dione (AD)/androsta-1,4-diene-3,17-dione (ADD), comprising the steps of: (a) heating sterols and an emulsifier respectively to dissolve completely and then mixing the dissolved sterols and emulsifier together to prepare a mixture wherein the emulsifier is selected from the group consisting of sucrose fatty acid ester, sorbitan fatty acid ester, polysorbate, polyglycerol fatty acid, propylene glycerol fatty acid and polyglycerine fatty acid ester; (b) placing the mixture in a water bath at 70–90° C. and stirring the mixture to obtain emulsified sterols; (c) adding the emulsified sterols to a culture media comprising *Mycobacterium fortuitum* EUG-119 (KCCM-10259) as a component of the media, and culturing *Mycobacterium fortuitum* EUG-119 (KCCM-10259) to produce androst-4-ene-3,17-dione (AD)/androsta-1,4-diene-3,17-dione (ADD); and (d) recovering said androst-4-ene-3,17-dione (AD)/androsta-1,4-diene-3,17-dione (ADD) from the culture.

2. The method as set forth in claim 1, wherein the sterols and emulsifier are mixed at a weight ratio of 1:0.2–2.0 (w/w).

3. The method as set forth in claim 1, wherein the emulsified sterols are added to the culture media at a weight of 0.01–10 g per 100 ml of the culture media.

4. The method as set forth in claim 1, wherein the sterols are selected from the group consisting of cholesterol, sitosterol, campesterol, stigmasterol and ergosterol.

* * * * *